United States Patent

Cornelius et al.

[11] Patent Number: 5,810,265
[45] Date of Patent: Sep. 22, 1998

[54] ELECTROSTATIC SPRAYING DEVICE

[75] Inventors: Gay Joyce Cornelius, North Humberside; Timothy James Noakes; Andrew Jefferies, both of Nr. Mold, Clywd; Michale Leslie Green, Nannerch, Clywd; Maurice Joseph Prendergast, Runcorn, all of United Kingdom

[73] Assignee: Reckitt & Colman Products Limited, London, United Kingdom

[21] Appl. No.: 793,437

[22] PCT Filed: Sep. 6, 1995

[86] PCT No.: PCT/GB95/02108

§ 371 Date: May 5, 1997

§ 102(e) Date: May 5, 1997

[87] PCT Pub. No.: WO96/07484

PCT Pub. Date: Mar. 14, 1996

[30] Foreign Application Priority Data

Sep. 7, 1994 [GB] United Kingdom .................... 9418039

[51] Int. Cl.⁶ ....................................................... B05B 5/16
[52] U.S. Cl. .............................. 239/690; 239/44; 239/601
[58] Field of Search ................................ 239/690, 34, 44, 239/145, 601, 708

[56] References Cited

U.S. PATENT DOCUMENTS

| | | | |
|---|---|---|---|
| 4,341,347 | 7/1982 | De Vittorio | 239/3 |
| 5,176,321 | 1/1993 | Doherty | 239/3 |
| 5,196,171 | 3/1993 | Peltier | 422/121 |
| 5,337,963 | 8/1994 | Noakes | 239/690 |
| 5,382,410 | 1/1995 | Peltier | 422/121 |

FOREIGN PATENT DOCUMENTS

| | | |
|---|---|---|
| 029 302 | 5/1981 | European Pat. Off. . |
| 120 633 | 10/1984 | European Pat. Off. . |
| 195 546 | 9/1986 | European Pat. Off. . |
| 243 031 | 10/1989 | European Pat. Off. . |
| 394 222 | 10/1990 | European Pat. Off. . |
| 441 501 | 8/1991 | European Pat. Off. . |
| 468 735 | 1/1992 | European Pat. Off. . |
| 468 736 | 1/1992 | European Pat. Off. . |
| 470 712 | 2/1992 | European Pat. Off. . |
| 482 814 | 4/1992 | European Pat. Off. . |
| 486 198 | 5/1992 | European Pat. Off. . |
| 501 725 | 9/1992 | European Pat. Off. . |
| 503 766 | 9/1992 | European Pat. Off. . |
| 523 962 | 1/1993 | European Pat. Off. . |
| 2 022 418 | 12/1979 | United Kingdom . |
| 2 030 060 | 4/1980 | United Kingdom . |
| 2 061 769 | 5/1981 | United Kingdom . |
| 2 092 025 | 8/1982 | United Kingdom . |
| 91/16990 | 11/1991 | WIPO . |
| 92/12798 | 8/1992 | WIPO . |
| 93/06937 | 4/1993 | WIPO . |
| 95/06521 | 3/1995 | WIPO . |
| 95/08396 | 3/1995 | WIPO . |

*Primary Examiner*—Lesley D. Morris
*Attorney, Agent, or Firm*—Fish & Richardson P.C.

[57] ABSTRACT

An electrostatic spraying device for spraying liquids comprises a hollow capillary structure having a convoluted inner surface, one end of which contacts a reservoir of an electrostatically sprayable liquid preferably having a viscosity from 1 to $20 \times 10^{-6}$ m²/s and a volume resistivity from $2.5 \times 10^6$ to $5 \times 10^8$ ohm cm, the other end of which terminates in an atomization tip, and means for applying high voltage to the liquid in order to cause the liquid at the atomization tip to break up into a plurality of electrostatically charged droplets. Cartridges for use in the electrostatic spraying device are also described.

25 Claims, 2 Drawing Sheets

ELECTROSTATIC SPRAYING DEVICE

FIELD OF THE INVENTION

The present invention relates to an electrostatic spraying device and, in particular, to an electrostatic spraying device for dispensing liquid fragrances such as air fresheners or insecticides, or for other applications such as aromatherapy, air purification or for personal care applications, for example as an inhaler, or an aerosol applicator.

BACKGROUND OF THE INVENTION

Air freshening devices in which there is a slow release of vapor from a container containing a liquid air freshener are well known in the art.

Electrostatic devices for spraying liquids are also well known in the art. In such electrostatic spraying devices a liquid is drawn out preponderantly by electrostatic forces into ligaments which break up into electrically charged droplets.

WO-A-93/06937 discloses an electrostatic spraying device for spraying liquids comprising a nozzle in the form of a wick which is contacted with a reservoir containing the liquid to be sprayed. The wick is fabricated from a sheet of a resiliently deformable polymeric foam material of open celled structure and an edge of the sheet is profiled to form a plurality of sites at which liquid ligaments can be produced.

EP-A-0486198 discloses an electrostatic spraying device incorporating a cartridge containing a liquid, such as a fragrance producing oil, which is to be sprayed via a vertically disposed capillary structure, electric potential being applied to the liquid so that it is drawn across the end face of the capillary structure and is sprayed as a plurality of ligaments which break up into droplets.

We have now developed an electrostatic spraying device for dispensing liquids such as air fresheners, insecticides, aromatherapy oils or liquids for air purification in which a particular type of wick is used in combination with liquids of defined characteristics in order to provide a controlled atomization of the liquid from the tip of the wick.

SUMMARY OF THE INVENTION

Accordingly, the present invention provides an electrostatic spraying device which comprises:

(i) a reservoir of an electrostatically sprayable liquid;

(ii) a capillary structure which comprises a hollow tube having a convoluted inner surface and being formed of a polymeric material which is impermeable to the liquid, the capillary structure at one end contacting the reservoir of the liquid and at the other end terminating in an atomization tip, the capillary structure being such that when oriented substantially vertically and with the atomization tip uppermost, the capillary action is sufficient to transport the liquid to the outlet at the uppermost end of the tube; and (iii) means for applying high voltage to the liquid in order to cause the liquid to be projected from the atomisation tip as one or more ligaments and thereafter to break up into a plurality of electrically charged droplets.

The present invention also provides a cartridge for the storage of a liquid suitable for electrostatic spraying which comprises a cartridge body containing a reservoir of a liquid as defined above, a capillary structure as defined above and means for providing an electrical connection to a high voltage source. The means for providing an electrical connection to a high voltage source may comprise an electrical contact, or alternatively the cartridge may be at least partly formed from an electrically conducting or semi-conducting material.

DETAILED DISCLOSURE

The electrostatically sprayable liquid which forms the reservoir preferably has a volume resistivity of from $2.5 \times 10^6$ to $5 \times 10^8$ ohm cm, more preferably a volume resistivity of from $2.5 \times 10^7$ to $2.5 \times 10^8$ ohm cm. The liquid typically has a viscosity measured at 20° C. of 1 to 20 cst (1 to $20 \times 10^{-6}$ m$^2$/s), preferably a viscosity of 1 to 10 cst (1 to $10 \times 10^{-6}$ m$^2$/s), more preferably 1.5 to 4 cst (1.5 to $4 \times 10^{-6}$ m$^2$/s) and still more preferably 2 to 3 cst (2 to $3 \times 10^{-6}$ m$^2$/s). The liquid is preferably an air-freshener which is atomized by the electrostatic spraying device to fragrance the air in which the device is positioned, such as a room or corridor.

The electrostatically sprayable liquid is, however, generally a liquid which has a very low non-volatile resinous residue such that a volume of the liquid corresponding at least to the volume of the reservoir, preferably at least to twice the volume of the reservoir, can be dispensed without blocking the tube. Preferably the non-volatile resinous residue content of the liquid is less than 0.1% by weight.

The capillary structure used in the present invention comprises a hollow tube which preferably has a smooth outer surface. The hollow tube has a convoluted inner surface which is formed from a polymeric material which is impermeable to the liquid. It will be understood that for a capillary tube to be considered to be convoluted the ratio of the internal perimeter of the tube to the cross-sectional area is greater than 2/r where r is the radius of a circle having the same cross-sectional area as that of the convoluted tube in question. Preferably, the internal perimeter of the tube is equal to or greater than the external perimeter of the tube. The dimensions of the tube, the material from which it is fabricated and the properties of the liquid are so chosen that when the capillary structure is substantially vertically oriented with the atomization tip uppermost the liquid is drawn up the inside of the tube by capillary action to the atomisation tip. When an electrostatic charge is applied to the liquid in the reservoir the liquid at the atomization tip is drawn into ligaments and thereafter broken up into a plurality of electrically charged droplets.

The convoluted inner surface of the hollow tube may vary from structures in which simple rounded or pointed projections are directed into the lumen of the tube to more complex structures in which the projections may have interdigitating side branches. The convoluted inner surface of the tube contributes to the resistance to distortion of the tube during use.

A particularly preferred polymeric material from which the capillary structure may be formed is polyacetal, for example polyacetal PA-06010 manufactured by Aubex Corporation, Japan. The polymeric capillary tubes manufactured by Aubex Corporation are manufactured to a very high tolerance of ±5%, which is important for maintaining uniform flow rates from one device to the next. Other polymeric materials which may also be used are polyethylene, in particular high density polyethylene, polypropylene, polyethylene terephthalate, polyamide, poly(ether ether ketone), poly(ether sulphone) or poly(ether ketone).

The capillary structure preferably has an outer diameter in the range of from 0.1 to 1.5 mm, more preferably 0.4 to 0.8 mm, still more preferably about 0.6 mm.

The tip of the capillary structure is preferably planar and cut to an angle, typically of about 45°, to the axis of the hollow tube. The liquid to be atomized is brought to the atomisation tip by passive capillary action. It is then drawn out at the tip by electrostatic forces into ligaments which break up into electrostatically charged droplets. In order for this to happen the electric field strength must be sufficiently high and in order to reduce the voltage required to produce a sufficient field strength, it is known to supply the liquid to a sharp edge, the shape of which intensifies the electric field and from which the liquid is sprayed as a cloud of very small (micrometer) sized, charged droplets. The charged droplets are mutually repellant and have a very large surface area to volume ratio, thus resulting in rapid evaporation. The charged droplets seek to discharge on an earthed/grounded surface but remain suspended in the air as a cloud for long enough to influence large air spaces.

It is a particular advantage of the present invention that the capillary structures with the convoluted inner surfaces enable relatively low volumes of electrostatically charged liquids to be sprayed consistently over long periods of time of up to four weeks to eight weeks. The capillary structures with the convoluted inner surfaces possess a significant advantage over capillary tubes with smooth inner surfaces since they are less sensitive to bubble entrapment and hence the risk of interrupting electrical continuity through the liquid column to the tip. With a plain bore tube, a bubble of air entrapped, in the tube will be likely to separate the column of liquid into two parts, whilst with a convoluted tube it is unlikely, even if a bubble is entrapped, for the liquid column to be split into two parts. Thus, electrical continuity is maintained and the device can continue to spray. In addition, since the convoluted tube has a greater surface area in contact with the liquid than a plain bore tube, the capillary force available to force an entrapped bubble out of the tube is increased.

The means for applying a high voltage to the liquid preferably operates at a potential of from 2 to 25 kV, more preferably at a potential of from 8 to 15 kV and most preferably at a potential of from 10 to 12 kV.

In a preferred aspect of the present invention, for example when the device is to be used for air freshening, the means for applying an electrostatic charge to the liquid may be adapted for intermittent application. In this manner the electrostatic spraying device of the present invention may be operated intermittently, for example using an integral timer to switch the device into the operating mode with the application of the electrostatic charge to the liquid. Conveniently, the device of the present invention may be activated at 1 to 15 minute intervals, preferably 10 to 12 minutes, for a period of from 0.5 to 5 minutes, preferably 2 to 4 minutes, more preferably 3 minutes. In this manner, when the liquid is a fragrance, the perception of the air freshening effect achieved by the fragrance is enhanced. When the device is in its non operational mode the liquid fills the capillary tube and with the voltage switched off the meniscus of the liquid is located at the open end of the tube, but not at the leading extremity of the tube from which the liquid is atomized. When the voltage is applied, the liquid is drawn from the column filling the tube across the end face of the tube and is atomized from the atomisation tip of the tube. When the voltage is switched off, the liquid retracts so that the meniscus of liquid is again located within the tube where it is retained by surface tension forces. The device of the present invention, when adapted for intermittent use, is particularly advantageous since the liquid product and batteries have an extended life as compared to a device that continually emanates a fragrance or insecticide.

The present invention also includes within its scope an electrostatic spraying device which comprises a cartridge as hereinbefore defined, a housing into which the cartridge is adapted to be removably located with the capillary structure extending substantially vertically, and a high voltage source located within the housing for the application of an electrostatic potential to the electrical connection on the said cartridge. The high voltage source may comprise, for example, high voltage generating circuitry powered by a low voltage battery. The electrical connection on the cartridge may comprise an electrical contact extending through the base of the cartridge or, alternatively, the cartridge may be at least partly formed from an electrically conducting or semi-conducting material.

A particular advantage of the present invention is that the atomization tip is arranged to spray generally vertically upwards without requiring a positive head. Preferably the cartridge of the present invention is designed so that there is a substantially constant head of liquid and the difference in liquid level between the full and the nearly empty levels does not significantly affect the charging of the liquid to the atomization tip.

One way of achieving a substantially constant head of liquid is for the cartridge to be of a generally squat configuration with a vertical dimension significantly less than its horizontal dimensions so that it can contact a significant amount of liquid while producing only a small change in liquid level between full and nearly empty conditions. Another way of achieving a constant head is disclosed in WO 95/06521.

For air freshening of a typical room the delivery of 0.3 grams of the liquid fragrance per day would provide a satisfactory level of fragrance. A cartridge containing 10 grams of the liquid fragrance would thus provide air freshening for one month.

The present invention will be further described with reference to the accompanying drawings, in which.

Figure 1:
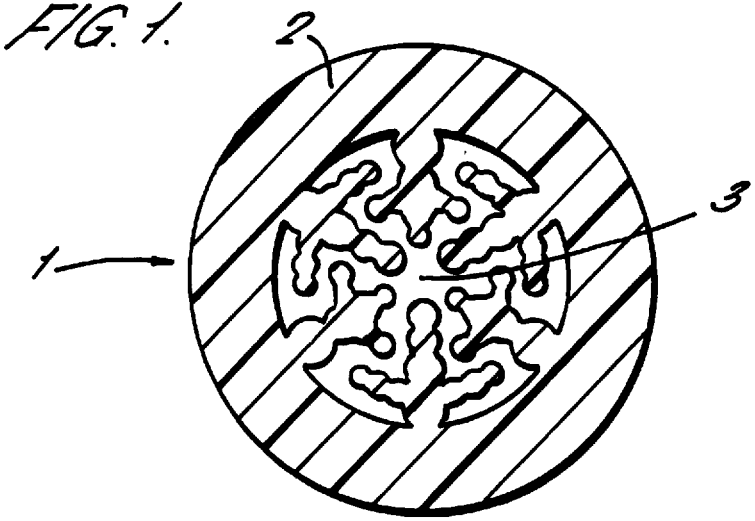
FIG. 1 is a cross section of a capillary structure for use in accordance with the invention.

Referring to the drawings, FIG. 1 illustrates in cross section, a capillary structure which is suitable for use in the present invention. The capillary structure is shown generally at 1 and is a cross section of a polyacetal hollow tube sold by Aubex Corporation of Japan, under the number PA-06010. The hollow tube, as shown in cross section, has a smooth outer surface 2 and a convoluted inner surface 3. The tube has an outer diameter of 0.6 mm.

Figure 2A:
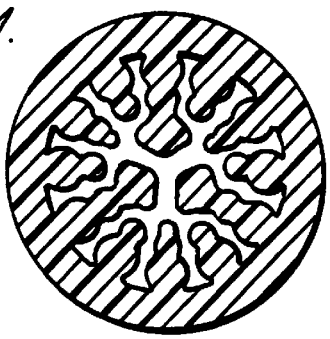
FIGS. 2A to 2H illustrate cross sections of other capillary structures for use in accordance with the invention.
Figure 2B:
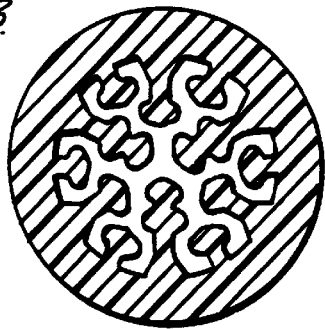
Figure 2C:
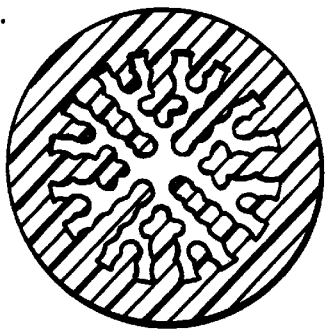
Figure 2D:
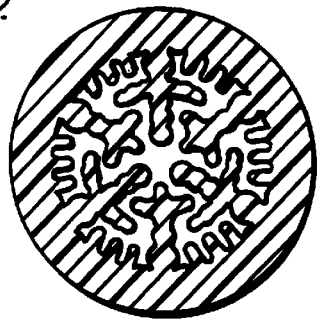
Figure 2E:
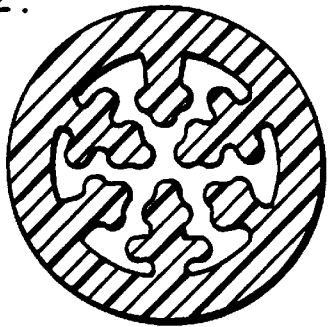
Figure 2F:
Figure 2G:
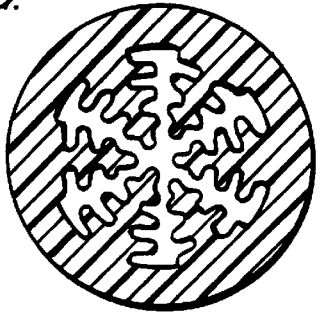
Figure 2H:
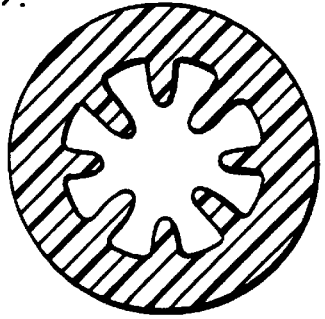

FIGS. 2A to 2H illustrate the cross sections of alternative capillary structures which have convoluted inner surfaces. As can be seen from these drawings, the convoluted inner surfaces may be of a relatively simple design as shown in FIG. 2H, or of more complex design as shown in the other Figures.

Figure 3:
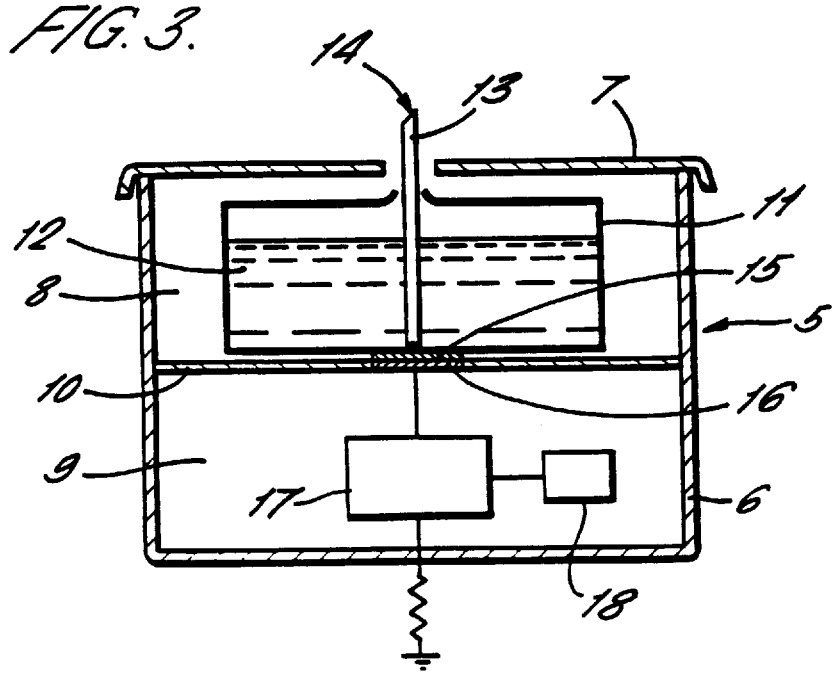
FIG. 3 is a schematic view of an electrostatic spraying device in accordance with the present invention.

FIG. 3 illustrates an electrostatic spraying device comprising a housing 5, which consists of a body portion 6 and a removable lid or cover 7. The housing is divided into two separate compartments, an upper compartment 8 and a lower compartment 9, by means of an inner wall 10. The upper compartment houses a cartridge 11 which contains a reservoir of an air freshener liquid 12 therein. A hollow capillary tube 13 of the type as described with reference to FIG. 1 is positioned within the liquid reservoir 12. The air freshener liquid wets the capillary structure 13 by passive capillary action so that liquid is present at the atomization tip 14 of the capillary structure 13. The base of the cartridge 11 has a connector 15 integrally formed therein. The cartridge rests upon the inner wall 10 of the housing immediately above a connector 16 which is formed in the said inner wall. A high voltage output is supplied from a high voltage generating circuitry 17, powered by a low voltage battery (not shown) via connections 16 and 15 to the air freshener liquid 12. The circuitry 17 is controlled by means of a timer 18 which is also housed in the lower portion of the housing.

When the timer is on, the high voltage is applied to the liquid air freshener 12 contained in the cartridge 11 to effect electrostatic spraying of the liquid from the atomization tip 14 of the hollow capillary structure 13. The timer may be, for example, operated for 3 minutes in every 15 minutes, i.e 4 times per hour. When the timer is off, the air freshener liquid will again wet the capillary structure 13 so that the atomization tip 14 contains air freshener liquid ready for electrostatic spraying when the timer is next in the on mode. It will be noted that the circuit has a connection to earth via the bottom wall of the housing body 6.

The cover 7 of the housing is fabricated from an electrically insulating plastics material such as polypropylene or polyethylene so that the cover does not immediately cause the electrostatic spray to earth. Liquid air freshener 12 contained in the container will meet the requirements of viscosity and volume resistivity as hereinbefore defined. Preferably the air freshener liquid will have a very low non-volatile resinous residue of less than 0.1% by weight, since otherwise any non-volatile material in the formulation will accumulate and interfere with the free-flow of the air freshener liquid, especially at the atomization tip. The air freshener liquid should also be free from any particulate material, since any particulates would interfere with the free-flow of liquid within the capillary structure. As previously described, the air freshener liquid rises to the upper open end of the capillary structure 13 by passive capillary action and under the influence of the applied high voltage (which may be negative or positive) is projected from the atomization tip as one or more ligaments which break up into particles which repel one another to form a cloud of atomized mist. The particles are drawn away from the atomization tip towards any objects in the vicinity of the device which are at earth potential.

It will be noted that the cartridge 11, containing the air freshener liquid is relatively squat and this enables the air freshener liquid to be drawn into the capillary structure by passive capillary action. without the height of the liquid in the container having much effect on the performance. When the air freshener cartridge is spent, then the lid 7 of the housing may be removed and a new cartridge inserted ready for use.

We claim:

1. An electrostatic spraying device which comprises:
   (i) a reservoir of an electrostatically sprayable liquid;
   (ii) a capillary structure which comprises a hollow tube having a convoluted inner surface and being formed of a polymeric material which is impermeable to the liquid, the capillary structure at one end contacting the reservoir of the liquid and at the other end terminating in an atomization tip, the capillary structure being such that when oriented substantially vertically and with the atomisation tip uppermost, the capillary action is sufficient to transport the liquid to the outlet at the uppermost end of the tube; and
   (iii) means for applying high voltage to the liquid in order to cause the liquid to be projected from the atomization tip as one or more ligaments and thereafter to break up into a plurality of electrically charged droplets.

2. An electrostatic spraying device as claimed in claim 1 wherein the electrostatically sprayable liquid has a viscosity in the range of from 1 to 20 cst (1 to $20 \times 10^{-6}$ m$^2$/s) at a temperature of 20° C. and a volume resistivity of from $2.5 \times 10^6$ to $5 \times 10^8$ ohm cm.

3. An electrostatic spraying device as claimed in claim 2, wherein the liquid has a viscosity in the range of from 1.5 to 4 cst (1.5 to $4 \times 10^{-6}$ m$^2$/s) at a temperature of 20° C.

4. An electrostatic spraying device as claimed in claim 2 wherein the liquid has a volume resistivity of $2.5 \times 10^7$ to $2.5 \times 10^8$ ohm cm.

5. An electrostatic spraying device as claimed in claim 1 wherein the capillary structure has a smooth outer surface.

6. An electrostatic spraying device as claimed in claim 1 wherein the liquid is substantially free from any non-volatile resinous.

7. An electrostatic spraying device as claimed in claim 5 wherein the capillary structure is formed from polyacetal, polypropylene, polyethylene, polyethylene terephthalate, polyamide, poly(ether ether ketone), poly(ether sulphone) or poly(ether ketone).

8. An electrostatic spraying device as claimed in claim 7 wherein the capillary structure has an outer diameter in the range of from 0.1 to 1.5 mm.

9. An electrostatic spraying device as claimed in claim 8 wherein the capillary structure has an outer diameter in the range of from 0.4 to 0.8 mm.

10. An electrostatic spraying device as claimed in claim 5 wherein the tip of the capillary structure is planar and cut at an angle, typically of about 45°, to the axis of the hollow tube.

11. An electrostatic spraying device as claimed in claim 1 wherein the means for applying a high voltage to the liquid is adapted for intermittent application.

12. An electrostatic spraying device as claimed in claim 11 wherein the means for applying a high voltage to the liquid operates at a potential of from 2 to 25 kV.

13. A cartridge for the storage of a liquid suitable for electrostatic spraying, which cartridge comprises:
    (a) a cartridge body containing a reservoir of an electrostatically sprayable liquid;
    (b) a capillary structure which comprises a hollow tube having a convoluted inner surface and being formed of a polymeric material which is impermeable to the liquid, the capillary structure at one end contacting the reservoir of the liquid and at the other end terminating in an atomization tip, the capillary structure being such that when oriented substantially vertically and with the atomization tip uppermost, the capillary action is sufficient to transport the liquid to the atomization tip; and
    (c) means for providing an electrical connection to a high voltage source.

14. A cartridge as claimed in claim 13 wherein the electrostatically sprayable liquid has viscosity in the range of from 1 to 20 cst (1 to $20 \times 10^{-6}$ m$^2$/s) at a temperature of 20° C. and a volume resistivity of from $2.5 \times 10^6$ to $5 \times 10^8$ ohm cm.

15. A cartridge as claimed in claim 14, wherein the liquid has a viscosity in the range of from 1.5 to 4 cst (1.5 to $4 \times 10^{-6}$ m$^2$/s) at a temperature of 20° C.

16. A cartridge as claimed in claim 14 wherein the liquid has a volume resistivity of $2.5 \times 10^7$ to $2.5 \times 10^8$ ohm cm.

17. A cartridge as claimed in claim 13 wherein the capillary structure has a smooth outer surface.

18. A cartridge as claimed in claim 13 wherein the liquid is substantially free from any non-volatile resinous constituent.

19. A cartridge as claimed in claim 17 wherein the capillary structure is formed from polyacetal, polypropylene, polyethylene, polyethylene terephthalate, polyamide, poly(ether ether ketone), poly(ether sulphone) or poly(ether ketone).

20. A cartridge as claimed in claim 19 wherein the capillary structure has an outer diameter in the range of from 0.1 to 1.0 mm.

21. A cartridge as claimed in claim 20 wherein the capillary structure has an outer diameter in the range of from 0.4 to 0.8 mm.

22. A cartridge claimed in claim 17 wherein the tip of the capillary structure is planar and cut at an angle, typically of about 45°, to the axis of the hollow tube.

23. A cartridge as claimed in claim 13 wherein the high voltage source operates at a potential of from 2 to 25 kV.

24. An electrostatic spraying device which comprises a cartridge comprising (a) a cartridge body containing a reservoir of an electrostatically spraying liquid, (b) a capillary structure which comprises a hollow tube having a convoluted inner surface and being formed of a polymeric material which is impermeable to the liquid, the capillary structure at one end contacting the reservoir of the liquid and at the other end terminating in an atomization tip, the capillary structure being such that when oriented substantially vertically and with the atomization tip uppermost, the capillary action is sufficient to transport the liquid to the atomisation tip, and (c) means for providing an electrical connection to a high voltage source;

a housing into which the cartridge is adapted to be removably located with the capillary structure extending in a substantially vertical direction; and the high voltage source located within the housing for application of an electrostatic potential to the electrical connection on said cartridge.

25. An electrostatic spraying device as claimed in claim 24, wherein the high voltage source comprises high voltage generating circuitry located within the housing.

* * * * *

UNITED STATES PATENT AND TRADEMARK OFFICE
CERTIFICATE OF CORRECTION

PATENT NO. : 5,810,265

DATED : September 22, 1998

INVENTOR(S) : Gay Joyce CORNELIUS; Timothy James NOAKES; Andrew JEFFERIES; Michael Leslie GREEN; and Maurice Joseph PRENDERGAST It is certified that error appears in the above-identified patent and that said Letters Patent is hereby corrected as shown below:

On the cover page, under "[75] Inventors", delete "Michale" and insert --Michael--.

Signed and Sealed this

Twenty-sixth Day of January, 1999

Attest:

Attesting Officer

*Acting Commissioner of Patents and Trademarks*

UNITED STATES PATENT AND TRADEMARK OFFICE
CERTIFICATE OF CORRECTION

PATENT NO.    : 5,810,265

DATED         : 22 September 1998

INVENTOR(S)   : Gay Joyce CORNELIUS; Timothy James NOAKES; Andrew JEFFERIES; Michael Leslie GREEN; and Maurice Joseph PRENDERGAST It is certified that error appears in the above-identified patent and that said Letters Patent is hereby corrected as shown below:

On the cover page, under "[73] Assignee:", add --Imperial Chemical Industries plc, London, United Kingdom--.

Signed and Sealed this

Sixteenth Day of November, 1999

Attest:

Q. TODD DICKINSON

*Attesting Officer*  *Acting Commissioner of Patents and Trademarks*